United States Patent [19]

Verbeek

[11] Patent Number: 5,690,613

[45] Date of Patent: Nov. 25, 1997

[54] RAPID EXCHANGE HIGH PRESSURE TRANSITION FOR HIGH PRESSURE CATHETER WITH NON-COMPLIANT BALLOON

[75] Inventor: Maurice T.Y. Verbeek, Geleen, Netherlands

[73] Assignee: Medtronic, Inc., Minneapolis, Minn.

[21] Appl. No.: 759,696

[22] Filed: Dec. 6, 1996

[51] Int. Cl.$^6$ .................................................. A61M 29/00
[52] U.S. Cl. ........................... 604/103; 604/96; 606/194
[58] Field of Search ........................... 604/96–104, 282; 128/898; 606/191–200, 108; 600/201, 204, 207

[56] References Cited

U.S. PATENT DOCUMENTS

| | | | |
|---|---|---|---|
| 4,655,746 | 4/1987 | Daniels et al. | 604/53 |
| 4,748,982 | 6/1988 | Horzewski et al. | |
| 4,762,129 | 8/1988 | Bonzel | |
| 4,771,777 | 9/1988 | Horzewski et al. | |
| 5,040,548 | 8/1991 | Yock | |
| 5,061,273 | 10/1991 | Yock | 606/194 |
| 5,180,367 | 1/1993 | Kontos et al. | 604/101 |
| 5,242,396 | 9/1993 | Evard | 604/96 |
| 5,279,562 | 1/1994 | Sirhan et al. | 604/96 |
| 5,300,025 | 4/1994 | Wantink | 604/96 |
| 5,328,472 | 7/1994 | Steinke et al. | 604/102 |
| 5,364,376 | 11/1994 | Horzewski et al. | 604/280 |
| 5,410,797 | 5/1995 | Steinke et al. | |
| 5,451,233 | 9/1995 | Yock | 604/194 |
| 5,496,346 | 3/1996 | Horzewski et al. | 604/194 |
| 5,545,134 | 8/1996 | Hilaire et al. | 604/96 |
| 5,549,556 | 8/1996 | Ndondo-Lay et al. | 604/102 |
| 5,549,557 | 8/1996 | Steinke et al. | 604/103 |
| 5,567,203 | 10/1996 | Euteneuer et al. | 604/96 |

FOREIGN PATENT DOCUMENTS 9217236  10/1992  WIPO.

*Primary Examiner*—Glenn K. Dawson
*Attorney, Agent, or Firm*—Dianne M.F. Plunkett; Harold R. Patton

[57] ABSTRACT

A medical catheter is provided which includes a core wire extending longitudinally through inflation tubing. The inflation tubing defines an inflation lumen. The distal end of the inflation tubing extends longitudinally through a tubular first reinforcement band which terminates distal to the distal end of the inflation tubing. An inner lumen tube defines a guidewire lumen, the inner lumen tube being biaxial with the inflation tubing and running longitudinally along the outer diameter of the inflation tubing. The inner lumen tube extends longitudinally through a shim tube which has a longitudinal slit running along its top side. The inner lumen tubing which has the shim coaxially bonded thereon extends longitudinally through a shaft tube. The inflation tube with the first reinforcement band coaxially bonded thereon also extends longitudinally through the shaft tube. The shaft tube is bonded to the inner lumen tube and to the inflation tube. A metal piece may be bonded to the inflation tube. An inflatable balloon is mounted at the distal end of the shaft tube, the balloon is in fluid communication with the inflation lumen.

22 Claims, 3 Drawing Sheets

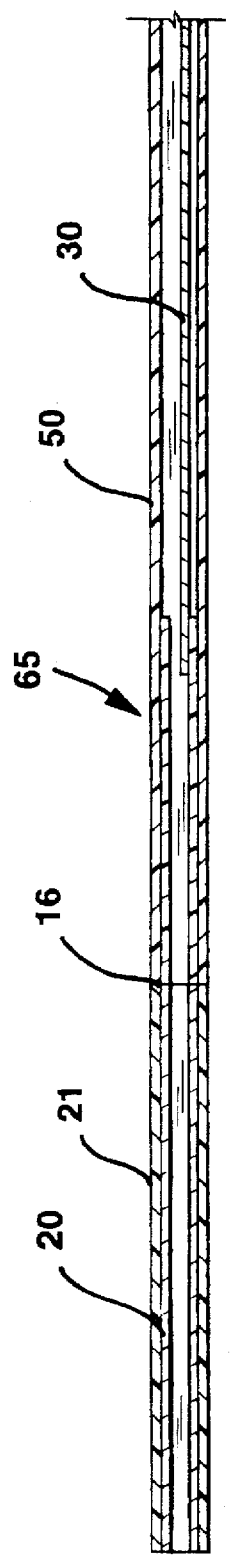
FIG.1A
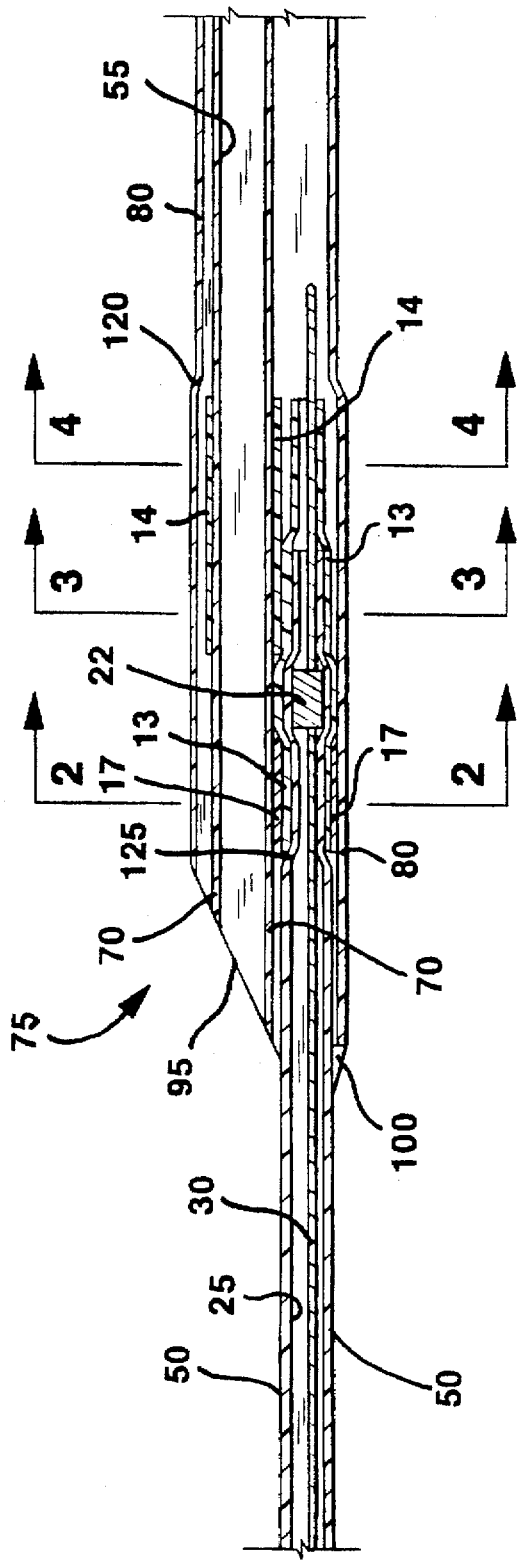
FIG. 1B
| FIG.1A | FIG.1B | FIG.1C |
FIG.1

RAPID EXCHANGE HIGH PRESSURE TRANSITION FOR HIGH PRESSURE CATHETER WITH NON-COMPLIANT BALLOON

FIELD OF THE INVENTION

The present invention relates to angioplasty catheters, and more particularly, to a shaft transition section for a rapid exchange high pressure balloon catheter.

BACKGROUND OF THE INVENTION

One of the therapeutic procedures applicable to the present invention is known as percutaneous transluminal coronary angioplasty (PTCA). This procedure can be used, for example, to reduce arterial build-up of .cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The original catheter can then be withdrawn and a catheter of a different size or another device such as an atherectomy device can be inserted.

Conventional angioplasty balloons fall into high, medium, and low pressure ranges. Low pressure balloons are those that have burst pressures below 6 atmospheres ($6.1 \times 10^5$ Pascals). Medium pressure balloons are those that have burst pressures between 6 and 12 atm ($6.1 \times 10^5$ and $1.2 \times 10^6$ Pa). High pressure balloons are those that have burst pressures above 12 atm ($1.2 \times 10^6$ Pa). Burst pressure is determined by such factors as wall thickness and tensile strength, for example.

High pressure balloons are desirable because they have the ability to exert more force and crack hard lesions. High pressure balloons are also useful in stent deployment. A biocompatible metal stent props open blocked coronary arteries, keeping them from reclosing after balloon angioplasty. A balloon of appropriate size and pressure is first used to open the lesion. The process is repeated with a stent crimped on a high pressure balloon. The stent is deployed when the balloon is inflated. A high pressure balloon is useful for stent deployment because the stent must be forced against the artery's interior wall so that it will fully expand thereby precluding the ends of the stent from hanging down into the channel encouraging the formation of thrombus.

Rapid exchange catheters are those which have shorter guidewire lumens passing from the distal end of the catheter through the balloon and opening to the exterior of the catheter somewhere proximal to the balloon. Catheter exchanges over the guidewire are easier to accomplish because they can be done with a single operator rather than two operators as required by over-the-wire catheters.

The catheter shaft area where the proximal end of the guidewire lumen begins is known as the transition area. Maintaining flexibility, a low profile and a strong bond in the transition area is difficult when high pressures of greater than 450 psi (31 bar) are used. With such pressures, parts could delaminate and separate. Typically, the area having the least bond strength, with the exception of the balloon area, is at the transition section where components meet and the tubing is necked down and/or weakened by heat.

U.S. Pat. Nos. 5,328,472 and 5,410,797 to Steinke et at. disclose flexible biaxial tubes which form the transition region. The rated burst pressure for this product is 10 bar with a transition area capable of 14 bar.

U.S. Pat. No. 5,545,134 to Hilaire et al. discloses a tube which comprises in its upper part a channel with a substantially circular cross-section which, once drawn, constitutes the second inner duct for the passage of a guide-wire, and in its lower part a second channel with a cross-section having substantially the shape of a crescent or kidney, which progressively disappears by stretching.

U.S. Pat. No. 5,549,556 to Ndondo-Lay et al in FIG. 6 and U.S. Pat. No. 5,549,557 to Steinke et al in FIG. 2 disclose a biaxial guidewire and inflation lumen. The inflation lumen being defined by a spring coil and an inflation lumen jacket with a central core wire. Such a transition construction withstands pressures of up to 400 psi.

What is needed is a rapid exchange catheter with a shaft transition that can reliably withstand internal pressure of at least 450 psi (31 bar) without leaking or rupturing which is relatively easy, consistent and reliable to manufacture.

SUMMARY OF THE INVENTION

The above features and advantages of the present invention, as well as others, are accomplished by providing a medical catheter comprising a core wire extending longitudinally through inflation tubing. The inflation tubing defines an inflation lumen. The distal end of the inflation tubing extends longitudinally through a tubular first reinforcement band which terminates distal to the distal end of the inflation tubing. An inner lumen tube defines a guidewire lumen, the inner tureen tube being biaxial with the inflation tubing and running longitudinally along the outer diameter of the inflation tubing. The inner lumen tube extends longitudinally through a shim tube which has a longitudinal slit running along its top side. The inner lumen tubing which has the shim coaxially bonded thereon extends longitudinally through a shaft tube. The inflation tube with the first reinforcement band coaxially bonded thereon also extends longitudinally through the shaft tube. The shaft tube is bonded to the inner lumen tube and to the inflation tube. A metal piece may be bonded to the inflation tube. An inflatable balloon is mounted at the distal end of the shaft tube, the balloon is in fluid communication with the inflation lumen.

BRIEF DESCRIPTION OF THE DRAWINGS

FIG. 1A is a longitudinal cross section of the proximal end of the shaft of the present invention;

FIG. 1B is a longitudinal cross-section of the transition section;

DETAILED DESCRIPTION OF THE PREFERRED EMBODIMENTS

Figure 1C:
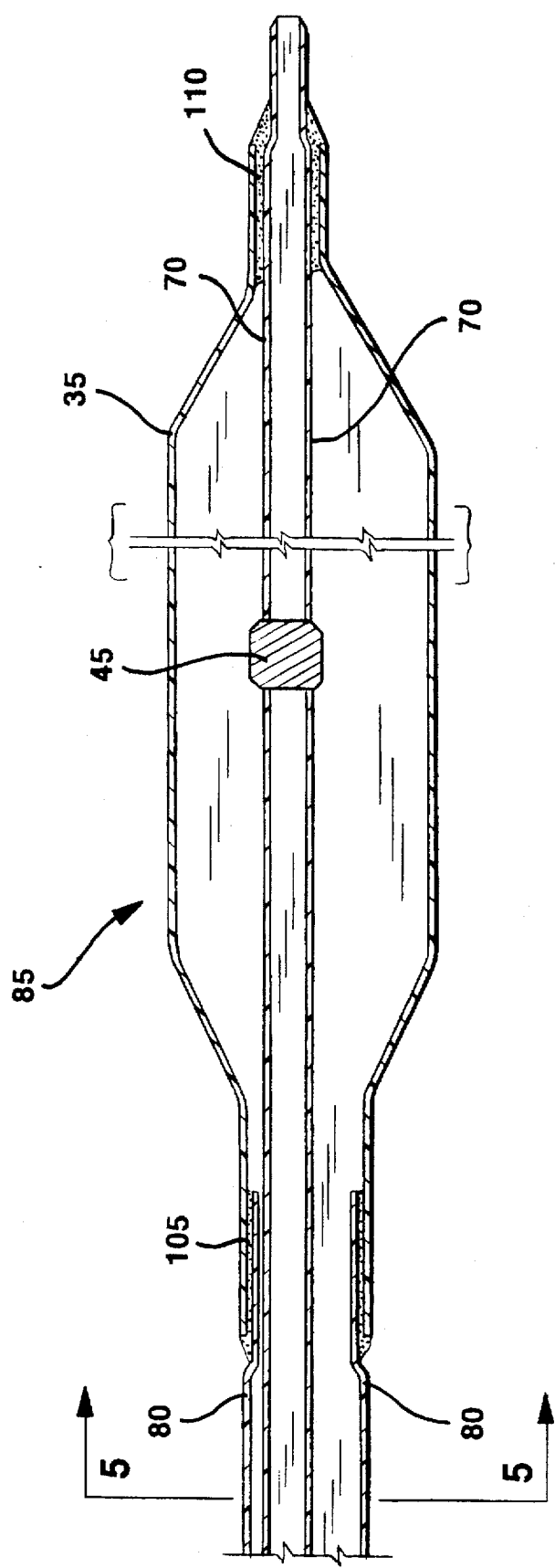
FIG. 1C is a longitudinal cross-section of the balloon.
Figure 3:
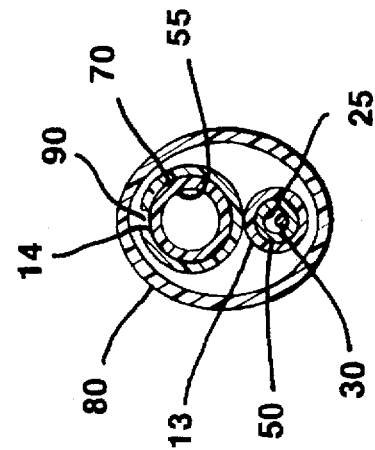
FIG. 3 is a cross-section taken along the lines 3—3 of FIG. 1B before heat shrinking.
Figure 5:
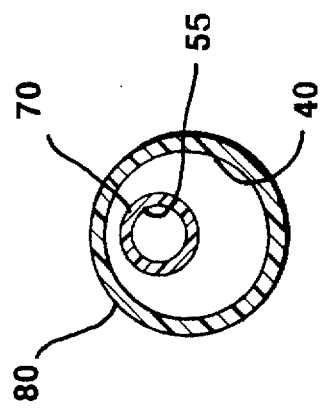
FIG. 5 is a cross-section taken along the lines 5—5 of FIG. 1C.
Figure 2:
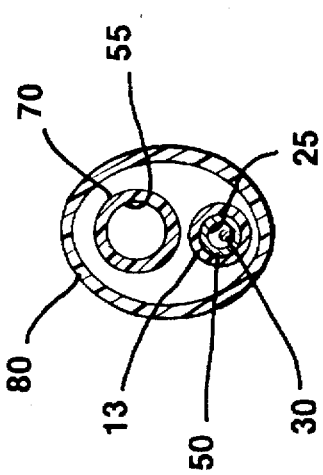
FIG. 2 is a cross-section taken along the lines 2—2 of FIG. 1B before heat shrinking.
Figure 4:
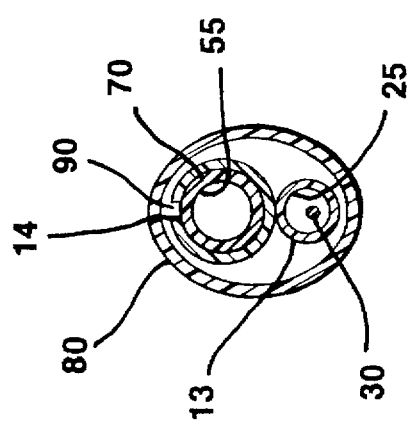
FIG. 4 is a cross-section taken along the lines 4—4 of FIG. 1B before heat shrinking.

The present invention provides a 6 French compatible, rapid exchange catheter with a transition that can reliably withstand internal pressure of at least 450 psi (31 bar) pressure without leaking or rupturing which is relatively easy, consistent and reliable to manufacture. FIG. 1A–1C are longitudinal cross-sectional views of a high pressure balloon catheter adapted for use in percutaneous transluminal coronary angioplasty (PTCA). FIG. 1A represents the proximal section 65. FIG. 1B represents the transition section 75. FIG. 1C represents the balloon section 85. With the addition of a metal piece such as a marker band 22, an irradiated reinforcement band of at least 8 mm in length and a shim 14 with a longitudinal slit 90 along the top side, the transition section 75 can withstand 2.44 Lbf or 10.8 N, which is over twice the typical catheter 5N minimum requirement.

The proximal section 65 of the shaft seen in FIG. 1A is made of a stainless steel 0.0232 inch (0.58 mm) outer diameter hypotube 20, a stainless steel core wire 30 tapering down from a 0.305 mm proximal end to a 0.102 mm distal end for flexibility, a 0.026 inch (0.66 mm) outer diameter clear laminate irradiated shaft tubing 21 and polyimide tubing 50 with essentially the same outer diameter as the shaft 21, or a minimal variance such as an 0.029 inch (0.74 mm) outer diameter. The distal end of the irradiated shaft tubing 21 is adhesively bonded to the proximal end of the polyimide tubing 50 using polyimide shaft adhesive 16.

The transition section 75 shown in FIG. 1B is designed to handle at least 450 psi (31 bar) pressure and still remain flexible enough to navigate torturous paths. The transition section 75 of the shaft seen in FIG. 1B adds the following components to the assembly, an exit marker band 22 made of radiopaque metal such as Pt/Ir or stainless steel, a reinforcement band 13 of a clear material such as irradiated Linear Low Density Polyethylene (LDPE), inner lumen tubing 70 defining a guidewire lumen made of High Density Polyethylene (HDPE), and an inner lumen shim 14 made of LDPE.

The balloon section 85 seen in FIG. 1C comprises distal shaft tubing 80 made of 50% HDPE/50% LDPE, a balloon 35 made of any material suitable for high pressures above 12 atm such as PET, PET blends or Nylon, and a balloon marker band 45 made of any suitable radiopaque metals such as platinum/iridium.

Begin the assembly process by preparing the polyimide tubing 50. Neck and trim the polyimide tubing 50 by inserting the distal end of polyimide tubing 50 having an outer diameter of 0.029 inches (0.74 mm) and an inner diameter of 0.0249 inches (0.63 mm) into the 0.022 inch diameter of the stepped mandrel. The stepped mandrel consists of a 0.022 inch outside diameter hypotube having an internal diameter to allow insertion of a 0.012 inch mandrel, which after insertion forms the stepped mandrel. Locate 9 mm of the tubing 50 onto the 0.012 inch section of the stepped mandrel.

Bonding a metal piece such as a marker band 22 into the transition section 75, and preferably to the inner diameter of the polyimide tubing 50 increases the pull strength of the transition section 75 thereby reducing the likelihood of separation under high inflation pressures. Greater force can be applied in the proximal direction without the polyimide tubing 50 separating from the reinforcement band 13. A radiopaque metal can be used for the marker band 22. This permits the marker band 22 to perform the function of allowing the physician to visualize with fluoroscopy the location of the guidewire exit at the proximal end of the inner lumen tubing 70. To accomplish the dual purpose of visualization and greater pull strength, slide an marker band 22 with an outside diameter of 0.56 mm and an inside diameter of 0.43 mm inside the polyimide tubing 50 and onto the 0.012 inch section of the stepped mandrel 5 mm distal from the distal end of the 0.022 inch section of the stepped mandrel. Pull back the 0.012 inch section mandrel far enough to be able to grasp the distal end of the tubing 50 with needle nose pliers. To anchor the marker band 22 within the transition section 75, perform necking by locating the tubing 50 which is over the 0.012 portion of the mandrel, over a heat source. Neck the distal end of the tubing 50 down to a 0.012 inch inner diameter for a trim length of 11.0 mm. This length is just long enough for anchoring and bonding. Trim the polyimide tubing 50 on the proximal side to a 20 cm length while inserted into a 0.022 inch mandrel.

Without a metal piece such as a marker band 22 in the transition section 75, the polyimide tubing 50 can be pulled out of the reinforcement band 13 with less effort because the weakest part of the bonding is between the polyimide tubing 50 and the reinforcement band 13. Adding the metal marker band 22 means that the marker band 22 must push aside all the material in the transition section 75 much like pulling a Ping-Pong ball through a tube with a smaller diameter than the diameter of the Ping-Pong ball.

Expand a 30 mm section of reinforcement band 13 to a diameter which is suitable for fitting over the polyimide tubing 50. The reinforcement band 13 must be irradiated to prevent the walls from melting and thinning. The wall formed by the reinforcement band 13 must be preserved because the wall from the inner lumen tubing 70 melts away and the reinforcement band 13 wall is then the last barrier for the pressure. For optimal pull strength the portion of the polyimide tubing 50 beyond the neck 125 where the reinforcement band 13 is crimped onto must be at least 10 mm. Testing showed reinforcement band 13 lengths of 6 mm was too short while a length of more than 12 mm was unnecessary. Locate the reinforcement band 13 over the distal end of the polyimide tubing 50 subassembly. Verify that the proximal end of the reinforcement band 13 is aligned with the polyimide tubing necking 125. The reinforcement band 13 will overlap the 0.433 inch (11 mm) length of the necked down distal end of the polyimide tubing 125, and will extend distally from the tubing 50 for a minimum length of 3 mm.

The distal end of the reinforcement band 13 will extend 0.315 inches (8 mm preferably with a range of 7 mm to 9 mm) beyond the distal end of the polyimide tubing 50. The proximal end of the reinforcement band 13 terminates at the neck 125 of the polyimide tubing so as to maintain a minimum profile. Using a heat source, shrink the reinforcement band 13 onto the polyimide tubing 50. The shim 14 length may range between approximately 9 mm and 11 mm. The distance between the polyimide tubing neck 125 and the distal end of the inner lumen shim 14 is approximately 0.748 inches (19.00 mm). The purpose of the inner lumen shim 14 is to fill the gap between the reinforcement band 13, inner lumen tubing 70 and distal shaft 80 distally from the exit marker band 22 and proximally from the distal shaft neck 120 with a material which has a melt compatibility with the material in both the LDPE reinforcement band 13 and the HDPE inner lumen tubing 70 so as to bond the pieces together and prevent leakage at high pressures.

Slit and trim the shim 14 into 10 mm lengths and cut a straight slit 90 from one end to the other. When positioned in the transition prior to melting, it is important that the slit 90 in shim 14 is on top. This is because melting shrinkage occurs in the opposite direction of the slit, i.e., downwards. The top of the distal shaft tubing 80 will shrink onto and bond with the top of the inner lumen tubing 70. The ends of the inner shim 14 (left and right from the slit 90) will pull down and fill in the cavities between the distal shaft tubing 80 and the inner tureen 70 and the reinforcement band 13. A mandrel in the guidewire lumen 55 and also in the inflation tureen 25 prevents these lumens from collapsing during heat shrinking and bonding of the transition section 75. The inflation/core wire lumen 25 empties into the inflation lumen 40 which is defined by the shaft 80. The inner lumen tubing 70 defines the guidewire lumen 55 and should have an inner diameter suitable for passing a standard 0.014 inch guidewire, as for example, 0.017 inches (0.43 mm). Neck the inner lumen tubing 70 within a 3 mm section to an outside diameter of approximately 0.457 mm to 0.559 mm. Cut the inner lumen tubing 70 to approximately 208–212 mm and preferably to 210 mm.

When no marker band 22 is used but adhesive is used to bond the polyimide tubing 50 to the reinforcement band 13 it is important that all surfaces are clean so as to reduce impurities contributing to separation failures. Clean and activate the surfaces with plasma treating. Ultraviolet (UV) curable adhesive could be used to bond the polyimide tubing 50 and reinforcement band 13 together. Put UV-curable adhesive on the polyimide tubing neck 125 and shrink the reinforcement band 13 around it. Cure the UV adhesive.

As seen in FIG. 1B, an optional second reinforcement band 17 with a length of 1.5 mm (0.06 inch) and a preshrunk wall thickness of 0.03 mm (0.001 inch), could also be placed proximal to the marker band 22 and coaxially over the proximal end of the reinforcement band 13. The second reinforcement band 17 would be placed proximal to the marker band 22 so that circumferential rigidity is increased. To increase the pull strength still further in the transition section 75, the material proximal to the marker band 22 could be made even more rigid. This can be done by using polyester tubing for the second reinforcement band 17. Polyester is more rigid than the LDPE. The second reinforcement band 17 could be used in conjunction with the marker band 22 or without the marker band 22. Pull strength is greatest with both the marker band 22 and the second reinforcement band 17. Pull strength is less with the marker band 22 only. Having the second reinforcement band 17 without the marker band 22 would not significantly increase pull strength. Omitting the marker band 22 simplifies manufacturing and reduces cost.

Assemble the distal shaft tubing 80 and the inner lumen tubing 70 as follows. Expand the proximal end of the distal shaft tubing 80 such that it will fit over the many layers of tubing within, including the inner lumen tubing 70, inner lumen shim 14, polyimide tubing 50, reinforcement band 13 and exit marker band 22. Assemble the shim 14 slit 90 face up onto the inner lumen tubing 70 such that the distal end of the shim 14 is 21.5 mm to 22.5 mm (0.846 inch to 0.886 inch) away from the proximal end of the inner lumen tubing 70. A mandrel with 0.0165 inch (0.42 mm) diameter is inserted in the inner lumen tubing 70. Locate the shim 14 assembly in the proximal end of the distal shaft 80 such that the distal end of the shim 14 is aligned with the distal shaft neck 120. Insert the two stepped mandrel of 0.022/0.012 inch inside the polyimide tubing 50 in such a way that the 0.012 section of the mandrel will extend from the distal end of the reinforcement band 13 with 5.0 to 10.0 mm (0.20 inch–0.39 inch). Insert the distal end of the polyimide tubing 50 into the proximal end of the distal shaft tubing 80. The distal end of the clear reinforcement band 13 preferably extends past the polyimide tubing 50 by 8 mm. Locate the distal end of the clear reinforcement band 13, in alignment with the distal end of the shim 14. After fitting the expanded distal shaft tubing 80 over these layers, heat shrink the distal shaft tubing 80 tightly down using a conventional heat source. The resulting distal shaft tubing 80 in the transition section 75 will have a major outer diameter of 0.048 inches (1.22 mm) and a minor outer diameter of 0.038 inches (0.97 mm).

Trim the excess proximal end of the distal shaft tubing 80 to just proximal to the proximal end of the inner lumen 70 tubing. Remove the 0.0163 inch mandrel from the transition section 75. Skive 95 the proximal end of the inner lumen tubing 70 at an angle of approximately 10 degrees for a length of 2 mm. Use a suitable medical grade cyanoacrylate adhesive such as Loctite® 420 preferably or 421 (manufactured by Loctite Corp. in Hartford Conn.) to create a polyimide shaft adhesive 100 fillet at the proximal end of the trimmed area of the inner lumen tubing 70 on the distal shaft tubing 80 perimeter. The purpose of the adhesive fillet 100 is to smooth the transition from the polyimide tubing 50 to the larger outer diameter of the distal shaft tubing 80 and to provide a secondary pressure seal for the inflation lumen 25. Remove the 0.022/0.012 inch stepped mandrel from the polyimide tubing 50.

Various visual markers can be applied onto the hypotube 20 and the polyimide shaft tubing 50. The markers can be used for physician end marks without the need for angiography; such end marks include the brachial approach or the femoral approach and the guidewire exit marker band 22. Markers should be approximately 2 mm to 4 mm wide around the polyimide tubing 50. Bond the balloon marker band 45 to the inner lumen tubing 70 using conventional adhesives.

Trim the balloon 35 tails to 2 mm at the distal neck end and to 4.5 mm at the proximal neck end. Neck down a 2 mm length of the distal end of the distal shaft tubing 80 for 1.5 mm diameter balloons. Balloons larger than a 1.5 mm diameter need not be necked down. Bonding surfaces may be treated to facilitate bonding. Bond the proximal balloon tail to the distal end of the distal shaft tubing 80 with any conventional manner such as adhesive 105. Bond the distal balloon tail to the distal end of the inner lumen tubing 70 with any conventional manner such as adhesive 110.

Prepare the hypotube assembly. Cut a hypotube 20 with an outer diameter of 0.0232 inches and an inner diameter of 0.010 to 0.012 inches to 42.13 inches in length. Braze the core wire 30 to the hypotube 20. The core wire 30 provides push and prevents the polyimide tubing 50 and transition area 75 from kinking when bent. Place the proximal end of the core wire 30 into the distal end of the hypotube 20 such that there is about a 7.0 mm to 9.0 mm overlap, and braze. Heat shrink the clear laminate irradiated shaft tubing 21 onto the hypotube and trim such that approximately 1.575 inches (40.0 mm) of the distal end of the hypotube 20 extends beyond the irradiated shaft tubing 21 on the distal end and approximately 50.0 mm extends on the proximal end. Insert the polyimide tubing 50 assembly onto the hypotube Align the core wire 30 through the transition section 75. Apply a suitable medical grade cyanoacrylate adhesive such as Loctite® 420 (manufactured by Loctite Corp. in Hartford Conn.) to the hypotube 20 and abut the proximal end of the polyimide tubing 50 with the distal end of the irradiated shaft tubing 21.

The preceding specific embodiments are illustrative of the practice of the invention. It is to be understood, however, that other expedients known to those skilled in the art or disclosed herein, may be employed without departing from the appended claims.

| No. | Component |
|---|---|
| 13 | First Reinforcement Band |
| 14 | Inner Lumen Shim |
| 16 | Polyimide Shaft Adhesive |
| 17 | Second Reinforcement Band |
| 20 | Hypotube |
| 21 | Irradiated Shaft Tubing |
| 22 | Marker Band |
| 25 | Core Wire Lumen/ Inflation Lumen |
| 30 | Core Wire |
| 35 | Balloon |
| 40 | Inflation Lumen |
| 45 | Balloon Marker Band |
| 50 | Polyimide Tubing |
| 55 | Guidewire Lumen |
| 65 | Proximal Section |
| 70 | Inner Lumen Tubing |
| 75 | Transition Section |
| 80 | Distal Shaft Tubing |
| 85 | Balloon Section |
| 90 | Slit |
| 95 | Skive |
| 100 | Adhesive Fillet |
| 105 | Proximal Bond Adhesive |
| 110 | Distal Bond Adhesive |
| 120 | Distal Shaft Neck |
| 125 | Polyimide Tubing Neck |

What is claimed is:

1. A medical catheter comprising:

a proximal section having a proximal end and a distal end;

a transition section having a proximal end and a distal end;

a balloon section having a proximal end and a distal end, the distal end of the proximal section being affixed to the proximal end of the transition section, the distal end of the transition section being affixed to the proximal end of the balloon section, the balloon section having a balloon mounted at the distal end, the transition section further comprising:

an inflation tube defining an inflation lumen, the inflation tubing having an inner diameter, an outer diameter, a proximal end and a distal end, the balloon being in fluid communication with the inflation lumen;

a first reinforcement band having a distal end and a proximal end, the distal end of the inflation tube extending longitudinally through the first reinforcement band, the distal end of the first reinforcement band terminating distal to the distal end of the inflation tube;

an inner lumen tube defining a guidewire lumen, the inner lumen tube being biaxial with the inflation tubing and running longitudinally along the outer diameter of the inflation tubing;

a shim tube, the inner lumen tube extending longitudinally through the shim tube, the shim tube having a proximal end and a distal end;

a shaft tube defining a shaft lumen; and the inner lumen tube having the shim tube coaxially bonded thereon extending longitudinally through the lumen of the shaft tube, the inflation tube with the first reinforcement band coaxially bonded thereon also extending longitudinally through the lumen of the shaft tube, the shaft tube being bonded to the inner lumen tube and to the inflation tube.

2. A catheter according to claim 1 wherein the inflation tube has a core wire extending longitudinally therethrough.

3. A catheter according to claim 1 wherein the shim tube has a longitudinal slit running along a top portion of the shim tube.

4. A catheter section according to claim 1 wherein the first reinforcement band is necked down over the distal end of the inflation tube such that the distal end of the shim tube is aligned with the distal end of the first reinforcement band.

5. A catheter according to claim 1 wherein the inflation tube is necked down proximal to the proximal end of the first reinforcement band, the necked down portion of the inflation tube abuts the proximal end of the first reinforcement band.

6. A catheter according to claim 1 wherein the shaft is necked down distal to and abutting the distal end of the shim.

7. A catheter according to claim 1 wherein a metal piece having a proximal end and a distal end is bonded to an inner surface of the inflation tube.

8. A catheter according to claim 7 wherein the proximal end of the shim tube is distal to the distal end of the metal piece.

9. A catheter according to claim 7 wherein the metal piece is made of a radiopaque material.

10. A catheter according to claim 1 wherein the first reinforcement band extends beyond the inflation tube by at least 5 mm.

11. A catheter according to claim 1 wherein the first reinforcement band is made of irradiated LDPE.

12. A catheter according to claim 1 wherein the shim tube is at least about 10 mm long.

13. A catheter according to claim 1 having a second reinforcement band, the second reinforcement band having a distal end and a proximal end, the inflation tube extending longitudinally through the second reinforcement band, the second reinforcement band distal end being proximal to the first reinforcement band proximal end.

14. A medical catheter comprising:

a proximal section having a proximal end and a distal end;

a transition section having the proximal end and a distal end;

a balloon section having a proximal end and a distal end, the distal end of the proximal section being affixed to the proximal end of the transition section, the distal end of the transition section being affixed to the proximal end of the balloon section, the balloon section having a balloon mounted at the distal end, the transition section further comprising:

an inflation tube, the inflation tube defining an inflation lumen, the inflation tube having an inner diameter, an outer diameter, a proximal end and a distal end, the balloon being in fluid communication with the inflation tube;

a first reinforcement band having a distal end and a proximal end, the distal end of the inflation tube extending longitudinally through a first reinforcement band, the distal end of the first reinforcement band terminating distal to the distal end of the inflation tube, the first reinforcement band being necked down over the distal end of the inflation tube, the inflation tube being necked down proximal to the proximal end of the first reinforcement band, the necked down portion of the inflation tube abutting the proximal end of the first reinforcement band;

an inner lumen tube defining a guidewire lumen, the inner lumen tube being biaxial with the inflation tubing and running longitudinally along the outer diameter of the inflation tubing;

a shim tube, the inner lumen tube extending longitudinally through the shim tube, the shim tube having a proximal end and a distal end, the distal end of the shim tube being aligned with the distal end of the first reinforcement band, the shim tube having a longitudinal slit running along a top portion of the shim tube;

a shaft tube defining a shaft lumen; and the inner lumen tube having the shim tube coaxially bonded thereon extending longitudinally through the shaft tube, the inflation tube with the first reinforcement band coaxially bonded thereon also extending longitudinally through the shaft tube, the shaft tube being bonded to the inner lumen tube and to the inflation tube, the shaft being necked down distal to and abutting the distal end of the shim tube.

15. A transition section according to claim 14 wherein a core wire extends longitudinally through the inflation lumen.

16. A transition section according to claim 14 wherein the first reinforcement band and the shim tube are made of LDPE.

17. A transition section according to claim 14 wherein the inner lumen tube is made of HDPE.

18. A transition section according to claim 14 wherein a metal piece is bonded to the inflation tube.

19. A transition section according to claim 14 wherein the proximal end of the shim tube is distal to the distal end of the metal piece.

20. A transition section according to claim 14 having a second reinforcement band, the second reinforcement band having a distal end and a proximal end, the inflation tube extending longitudinally through the second reinforcement band, the second reinforcement band distal end being proximal to the first reinforcement band proximal end.

21. A medical catheter comprising:

a proximal section, a balloon section and a transition section therebetween, the transition section further comprising:

a shaft tube;

inflation lumen means for fluid communication with the balloon section, the inflation lumen means within the shaft tube;

metal reinforcing means for interior reinforcement of the inflation lumen means;

band reinforcing means for exterior reinforcement of the inflation lumen means at a distal end of the inflation lumen means, the band reinforcing means bonded to the inflation lumen means and to the shaft tube;

guidewire lumen means within the shaft tube in side-by side relation with the inflation lumen means; and shim means for filling the space between the guidewire lumen means, the shaft tube and the band reinforcing means; the shim means bonded to the guidewire tureen means, the shaft tube and the band reinforcing means.

22. A method for making a medical catheter comprising the steps of:

providing an inflation lumen tube;

providing a reinforcing tube;

applying the reinforcing tube to the inflation lumen tube by shrinking the reinforcing tube into contact with an end of the inflation lumen tube;

providing a guidewire lumen tube;

providing a shim of material having a melting temperature which is less than the melting temperature of the guidewire lumen tube and less than the melting temperature of the reinforcing tube;

applying the shim around the guidewire lumen tube;

providing a heat shrinkable shaft tube;

inserting the guidewire lumen tube and shim and the inflation lumen tube and reinforcing tube into the shaft tube; and heating the shaft tube to a temperature such that the shaft tube shrinks and the shim melts to bond the guidewire lumen tube, the shaft and reinforcing tube.

\* \* \* \* \*

UNITED STATES PATENT AND TRADEMARK OFFICE
CERTIFICATE OF CORRECTION

PATENT NO. : 5,690,613
DATED : Nov. 25, 1997
INVENTOR(S) : Maurice T.Y. Verbeek

It is certified that error appears in the above-identified patent and that said Letters Patent is hereby corrected as shown below:

C. 10 L. 11      "guidewire tureen" to be changed to "guidewire lumen"

Signed and Sealed this

Nineteenth Day of October, 1999

Attest:

Q. TODD DICKINSON

Attesting Officer     Acting Commissioner of Patents and Trademarks